United States Patent
Takasugi

[11] Patent Number: 5,924,181
[45] Date of Patent: Jul. 20, 1999

[54] METHOD AND APPARATUS FOR CONSERVING A CADAVER

[75] Inventor: Mitsuo Takasugi, Kanagawa, Japan

[73] Assignee: Colpo Co., Ltd., Tokyo, Japan

[21] Appl. No.: 08/859,377

[22] Filed: May 20, 1997

[30] Foreign Application Priority Data

| May 21, 1996 | [JP] | Japan | 8-150071 |
| Aug. 6, 1996 | [JP] | Japan | 8-223050 |

[51] Int. Cl.⁶ .................................................. A61G 17/00
[52] U.S. Cl. ................................. 27/11; 62/78; 62/602; 62/603
[58] Field of Search ................. 27/11; 62/78, 64, 62/602, 603

[56] References Cited

U.S. PATENT DOCUMENTS

| 311,764 | 2/1885 | Johnson | 27/11 |
| 3,257,820 | 6/1966 | Case et al. | 27/11 |
| 3,693,371 | 9/1972 | Clark | 62/222 |
| 4,580,411 | 4/1986 | Orfitelli | 62/371 |
| 4,773,230 | 9/1988 | Garrett | 62/237 |
| 5,689,961 | 11/1997 | Cosman | 62/78 |

*Primary Examiner*—John G. Weiss
*Assistant Examiner*—Dennis Ruhl
*Attorney, Agent, or Firm*—Browdy and Neimark

[57] ABSTRACT

In the method, cadaver (50) is kept at low temperature and sterilized in casket (1, 2) or disaster pouch (51), which prevents cadaver (50) from putrefying and bacteria from propagating therein. In the apparatus, casket (1, 2) constructed of casket body (1) and lid (2). Disposed in casket (1, 2) is cooling means constructed of: cooling casing (3, 8); nozzle (20) for supplying a liquefied cooling gas to cooling casing (3, 8). One or a plurality of ventilation boards (4, 9) are incorporated in casing (3, 8) wherein cooling chamnber (6, 11) is formed between board (4, 9) and casing (3, 8) to permit the cooling gas to enter board (4, 9) and flow in a direction opposite to that of the gas flowing inside the cooling chamber (6, 11).

10 Claims, 8 Drawing Sheets

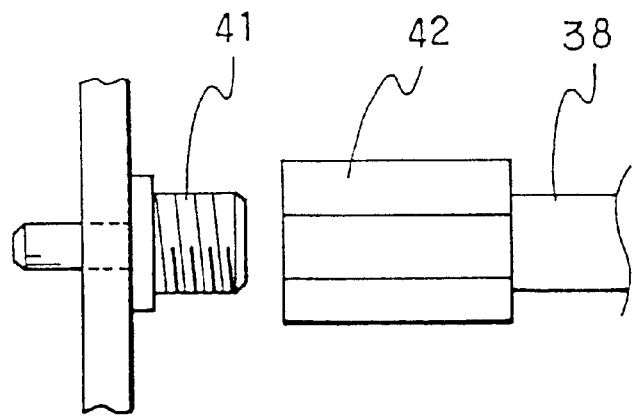
F I G. 6 (A)
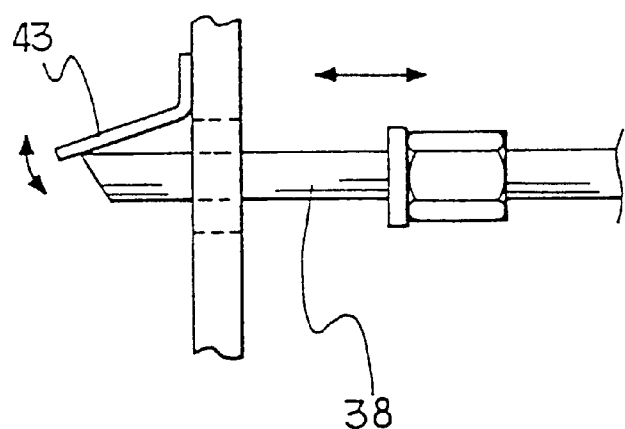
F I G. 6 (B)

METHOD AND APPARATUS FOR CONSERVING A CADAVER

BACKGROUND OF THE INVENTION

1. Field of the Invention

The present invention relates to a method and apparatus for conserving a cadaver, and more particularly to a method and apparatus for conserving a cadaver, wherein: the apparatus forms a container such as caskets, corpse containing disaster pouches and the like; the interior of the container is kept at a low temperature and also sterilized to prevent the cadaver from putrefying so as to be free from any obnoxious odors, and to prevent bacteria from propagating therein; and, the inside of the cadaver is cleaned and cooled so that the cadaver is conserved for a long period of time.

2. Description of the Prior Art

In general, a casket and like corpse containing means is cooled to prevent a cadaver from putrefying so as to be free from obnoxious odors. In order to cool the cadaver, it is conventional to use a suitable cooling means such as dry ice, electric coolers and like cooling means. Of these cooling means, dry ice is the most simple means for cooling the cadaver. However, dry ice has a distinct drawback because of its difficulty in temperature control, which often causes a partial freeze of the cadaver.

On the other hand, as for the electric coolers, it is necessary to provide such electric cooler in each of the caskets. However, the casket provided with the electric cooler is costly, and, therefore disadvantageous from the economical point of view. In addition, this type of casket is noisy in operation, and difficult in temperature control when disconnected from its electric cooler. Further, in transportation, this type of casket may lack a power supply. There is another method for cooling the casket, which uses an electronic cooler, for example such as Peltier devices, and, therefore costly and poor in cooling power. Since the casket using the electric or electronic cooler comprises non-burning materials, it is necessary to replace the casket's lid comprising such non-burning materials with a combustible lid before the casket is carried out of the house, which often takes much time and labor.

When the casket containing the cadaver is carried out of the house, the family of the deceased often touches the cadaver, which facilitates propagation of bacteria especially in hot weather. Consequently, in case that the cadaver is, contaminated with contagium, it is highly possible that the family thus touched the cadaver takes a direct infection of such contagium. However, in the prior art, there is no idea of positive sterilization of bacteria which contaminate the cadaver and the vicinity thereof.

Further, in Europe and other reunions, in order to retain the appearance of the live person as to a dead body, a so-called "embalming" has been extensively used. Embalming is an operation in which an incision is first formed in each of a carotid artery, i.e., principal artery in a neck; portion and another principal artery in a groin portion of the dead body; and, then an antiseptic solution, which is colored red, is injected into the dead body through the incision formed in the neck portion and the blood drained from the dead body together with the thus injected antiseptic solution through the other incision formed in the groin portion of the dead body, so that all the blood vessels are filled with the red antiseptic solution thus injected therein, which enables the dead body to retain the appearance of the live person. As for the abdomen of the dead body, it is also possible to apply embalming to the body by removing the viscera thereof and injecting the red antiseptic solution in place of the viscera. However, such embalming of the abdomen requires extremely sophisticated techniques, and, is therefore very expensive. For example, a typical facility for such embalming costs more than a hundred million yen in installation, and is therefore rare even in Europe and other regions.

As described above, the conventional method and apparatus for conserving the cadaver are causing many problems.

SUMMARY OF THE INVENTION

It is an object of the present invention to provide a method and apparatus for conserving a cadaver, which are free from any problems inherent in the prior art and applicable to the existing caskets and like corpse containing means in an easy manner, the method and apparatus using combustible materials adapted for cremation and being able to prevent the cadaver from freezing, in contrast with the case of dry ice in the prior art, by keeping the cadaver at moderate low temperatures in a sterilized condition to enable the cadaver to retain the appearance of the live person, the method and apparatus being able to prevent secondary infection of contagium.

It is another object of the present invention to provide a method and apparatus for conserving a cadaver with the appearance of the live person for a prolonged period, by applying a simple treatment to the cadaver substantially without damaging it.

According to a first aspect of the present invention, the above objects of the present invention are accomplished by providing:

A method for conserving a cadaver comprising the steps of:

forming a liquefied cooling-gas supply space in a casket or a corpse containing pouch; and supplying a liquefied cooling gas to the liquefied cooling-gas supply space;

whereby the interior of the casket or the corpse containing pouch is cooled and sterilized.

In the above method of the present invention, the liquefied cooling gas may be supplied to the liquefied cooling-gas supply space at predetermined time intervals. It is also possible to supply at a time a requisite amount of the liquefied cooling gas for conserving the cadaver for a predetermined period of time.

Further, in the above method of the present invention as set forth in the first aspect of the present invention, block-type dry ice, pellet-type dry ice, or, like cooling substance is disposed inside the casket or the corpse containing pouch to serve as an auxiliary cooling means.

According to a second aspect of the present invention, the above objects of the present invention are accomplished by providing:

In an apparatus for conserving a cadaver, comprising a casket and like means constructed of a casket body and its lid member in which a refrigerating mechanism is disposed, the improvement wherein:

the refrigerating mechanism is provided with a cooling casing; and a nozzle member for supplying a liquefied cooling gas to the interior of the cooling casing is connected with the cooling casing.

According to a third aspect of the present invention, the above objects of the present invention are accomplished by providing:

A method for conserving a cadaver comprising the step of:

injecting a liquefied cooling gas into the cadaver through its opening portion such as its oral cavity and the like. In general, liquefied carbon dioxide gas is used to produce a snow dry ice in the cadaver, whereby the cadaver is cleaned and conserved.

BRIEF DESCRIPTION OF THE DRAWINGS

FIG. 6(A) is an enlarged side view of an embodiment of the liquefied cooling-gas supply nozzle used in the another embodiment shown in FIG. 5;

FIG. 6(B) is an enlarged side view of another embodiment of the liquefied cooling-gas supply nozzle used in the another embodiment shown in FIG. 5;

DESCRIPTION OF THE PREFERRED EMBODIMENTS

Hereinbelow, the present invention will be described in detail with reference to the accompanying drawings.

Figure 1:
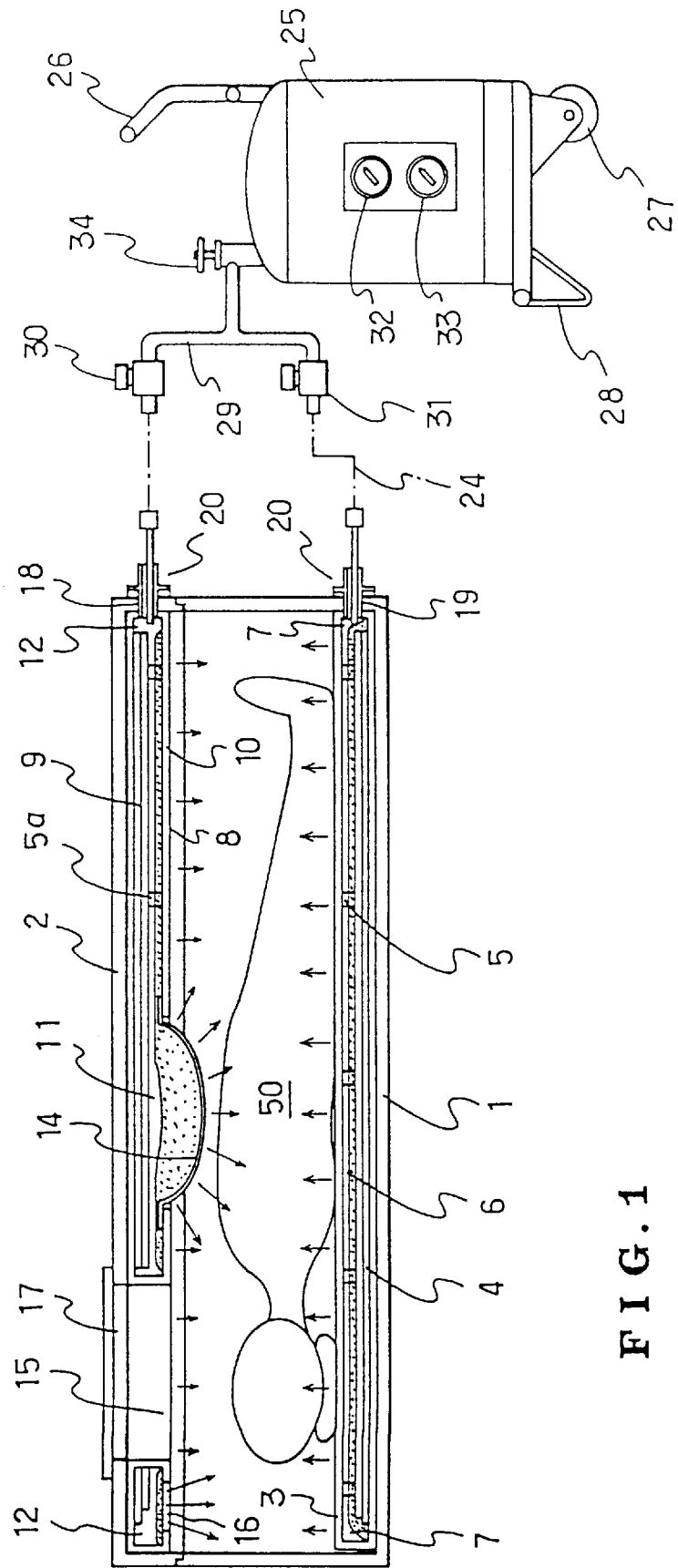
FIG. 1 is a schematic diagram of an embodiment of the apparatus of the present invention, partially illustrating a longitudinal section of the casket used in the apparatus.
Figure 2:
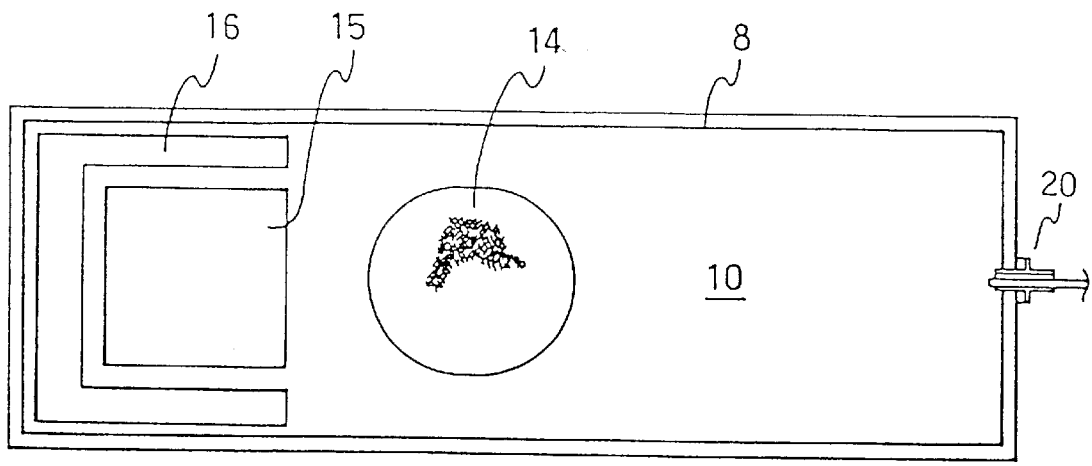
FIG. 2 is a bottom view of the bottom plate of the upper cooling casing used in the apparatus of the present invention shown in FIG. 1.

FIG. 1 shows a first embodiment of the present invention. As shown in FIG. 1, a refrigerating mechanism forming a refrigerating apparatus of the present invention may be incorporated in a casket and like corpse containing means (hereinafter simply referred to as the casket) when the casket is manufactured. It is also possible for the refrigerating mechanism of the present invention to be mounted in existing caskets. The casket used in the present invention may be conventional type constructed of a casket body 1 and its lid member 2, both of which is preferably made of combustible materials adapted for cremation, for example such as wood, plastics and the like. Mounted on an inner bottom surface of the casket body 1 is a lower cooling casing 3 made of combustible materials such as water-proof waxed papers, water-proof corrugated paperboards and like water-proof materials.

Figure 3:
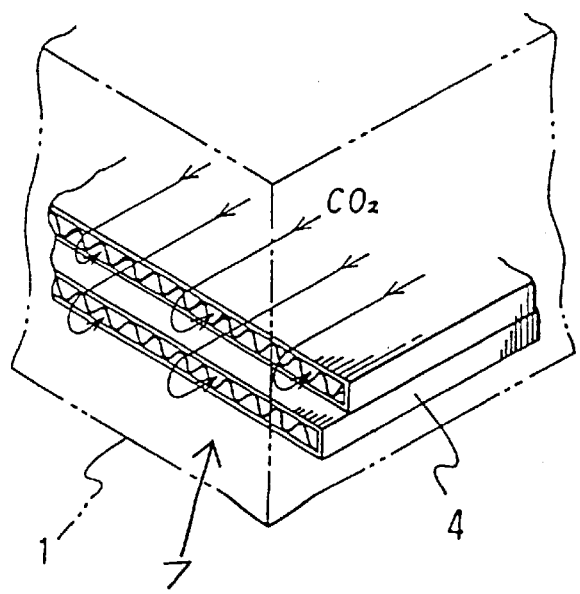
FIG. 3 is a perspective view of the ventilation board installed in the cooling casing of the apparatus of the present invention shown in FIG. 1 cooling gas flowing through the board.

A single or a multiple lower ventilation board 4, which has a permeable interior may be incorporated in the lower cooling casing 3. In this case, in order to produce a cooling chamber 6 to receive the cooling gas injected by supply tube 22 in a space above the lower ventilation board 4, a plurality of stay members 5 are preferably mounted wherein the upper plate of the lower cooling casing 3 and the lower ventilation board 4 so as to produce cooling chamber. Further, preferably, as shown in FIG. 3 the lower ventilation board 4 has a honeycomb construction because such construction is excellent in mechanical strength while also permitting flow of the $CO_2$ cooling gas from chamber 6 through ventilation board 4. As shown in FIG. 1, the lower ventilation board 4 has its opposite ends, i.e., its front and its rear ends be adjacent to a ventilation space 7. In other words, the opposite ends of the lower ventilation board 4 do not abut against the corresponding opposite ends of the cooling casing 3 so as to permit the cooling gas passing through the cooling chamber 6 over the lower ventilation board 4 to enter the interior of the ventilation board 4 through the end opposite the front end of the board 4 an leave the front end into gas recovery tube 21. This lower ventilation board 4 substantially serves as a heat insulating barrier from cooling chamber 6.

An upper cooling casing 8, which. is made of the same materials as those of the lower cooling casing 3, is mounted in the lid member 2. A single or a multiple upper ventilation board 9, which has the same construction as that of the lower ventilation board 4, is incorporated in the lid member 2 so as to abut against an upper inner surface of the upper cooling casing 8. In this case, in order to provide a cooling chamber 11 between a lower surface of the upper ventilation board 9 and a bottom plate 10 of the upper cooling casing 8, a plurality of stay members 5a are disposed on the bottom plate 10 of the cooling casing 8 and the ventilation board 9 in the same manner as that of the stay members 5. Further, a ventilation space 12 is provided in a position adjacent to each of opposite ends, i.e., front and rear ends of the upper ventilation board 9, which permits the cooling gas to pass through the cooling chamber 11 to enter the interior of the upper ventilation board 9 from the rear end and exit from the front end into gas recovery tube 21. This ventilation board 9 serves as a heat insulating barrier from cooling chamber 11 in the substantially same manner as that of the lower ventilation board 4.

Formed in a central area of the bottom plate 10 of the upper cooling casing 8 is an opening, which assumes a suitable shape such as circular, oval and any other shapes and corresponds in position to a torso portion of a cadaver 50. In this opening of the bottom plate 10, a snow reservoir 14 is fixedly mounted. The snow reservoir 14 is made of suitable permeable materials such as non-woven fabrics, nets and the like. In operation, as will be described later in detail, the liquefied cooling gas supplied to the cooling chamber 1 enters the snow reservoir 14, and is immediately transformed into snow, i.e., snow-like dry ice (hereinafter referred to the snow dry ice) in the reservoir 14. Then, the snow dry ice thus formed in the snow reservoir 14 supplies a cooling atmosphere to the cadaver 50 through its meshes or void portions.

If necessary, a window 15 for displaying a face portion of the cadaver 50 is formed in the bottom plate 10 of the upper cooling casing 8 at a position corresponding to the head portion of the cadaver 50. Formed around this window 15 is a cooling atmosphere supply hole 16 through which the cooling atmosphere moves downward. When the window 15 is provided, an opening 17 corresponding to the window 15 in position is so formed as to penetrate both of the upper ventilation board 9 and the lid member 2.

Formed in a side surface of the lid member 2 is a nozzle insertion hole 18 which communicates with the interior of the cooling chamber 11. Another nozzle insertion hole 19 is formed in a lower portion of a side surface of the casket body 1 and communicates with the interior of the cooling chamber 6. A nozzle 20 is hermetically inserted into each of these insertion holes 18, 19. In order to hermetically engage the nozzle 20 with these holes 18, 19 in an insertion manner, a suitable packing means is mounted on an inner peripheral surface of each of the insertion holes 18, 19 and/or on an outer peripheral surface of the nozzle 20. It is also possible to have the nozzle 20 and each of the insertion holes 18, 19 threadably engaged with each other.

Figure 4:
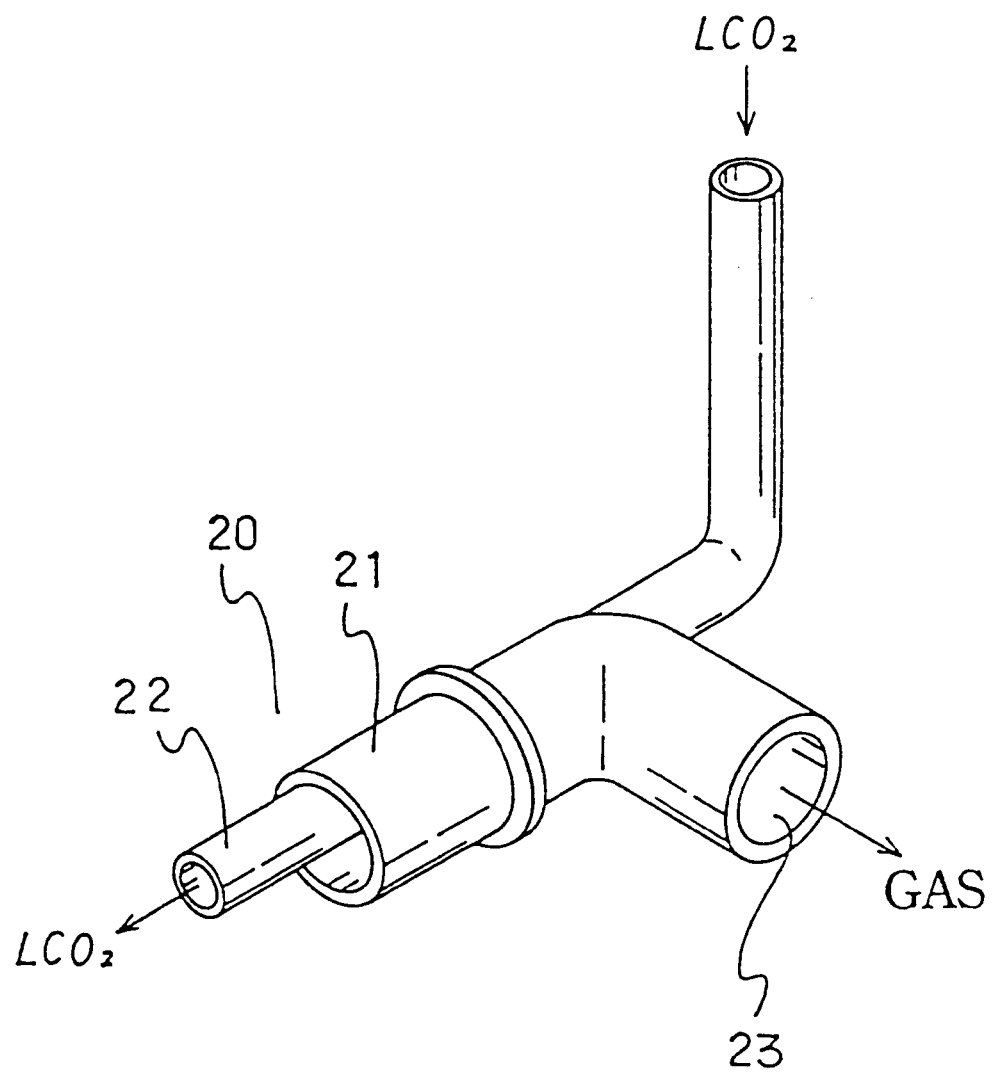
FIG. 4 is a perspective view of the liquefied cooling-gas supply nozzle used in the apparatus of the present invention shown in FIG. 1.

In general, as shown in FIG. 4, the nozzle 20 has a double-walled construction in which a liquefied cooling-gas supply tube 22 is housed in a gas recovery tube 21. The gas recovery tube 21 is provided with a gas discharge portion 23 through which the cooling gas having passed through the cooling chambers 6, 11 and respective ventilating boards 6 and 9 and thus collected is discharged to the atmosphere. Although not shown in the drawings, the gas discharge portion 23 is provided with a suitable filter element which also functions to sterilize bacteria. The liquefied cooling-gas supply tube 22 is connected with a liquefied cooling gas bomb 25 through a high pressure hose 24.

The gas bomb 25 is of a portable type provided with a grip 26, wheels 27 and a stand 28. Fixedly mounted on the gas bomb 25 are a pair of branch pipes 29 for supplying the liquefied cooling gas to the cooling chambers 6, 11. Each of the branch pipes 29 is provided with each of a pair of solenoid operated valves 30, 31. These valves 30 and 31 are controlled by timers 32 and 33, respectively. In FIG. 1, the reference numeral 34 denotes a stop valve.

In the apparatus of the present invention having the above construction, when the timers 32, 33 are operated so that the solenoid operated valves 30, 31 are opened, the liquefied cooling gas contained in the gas bomb 25 is injected into the cooling chambers 6, 11 through the high pressure hose 2 and the liquefied cooling-gas supply tubes 22. In general, liquefied carbon dioxide is used as the liquefied cooling gas so that the gas is transformed into a so-called snow dry ice immediately after injected into the cooling chambers 6, 11. Most of the snow dry ice thus formed is received and accumulated in the snow reservoir 14.

As a result, a cooling atmosphere is supplied to the torso portion of the cadaver 50 through the snow reservoir 14 and the bottom plate O of the upper cooling casing 8. When the cooling air supply hole 16 through which the cooling atmosphere moves downward is provided, a part of the liquefied cooling gas enters the interior of the casket body 1 to cool the head portion of the cadaver 50. The remaining gas enters the interior of the upper ventilation board 9 through the left one of the ventilation spaces 12 (as viewed in FIG. 1) to the cooling gas supply hole and flows to the right one of the ventilation spaces 12. The cooling gas issued from the right one of the ventilation spaces 12 is then received in the gas recovery tube 21 and discharged from the gas discharge portion 23 to the atmosphere through the suitable filter element (not shown).

Figure 10:
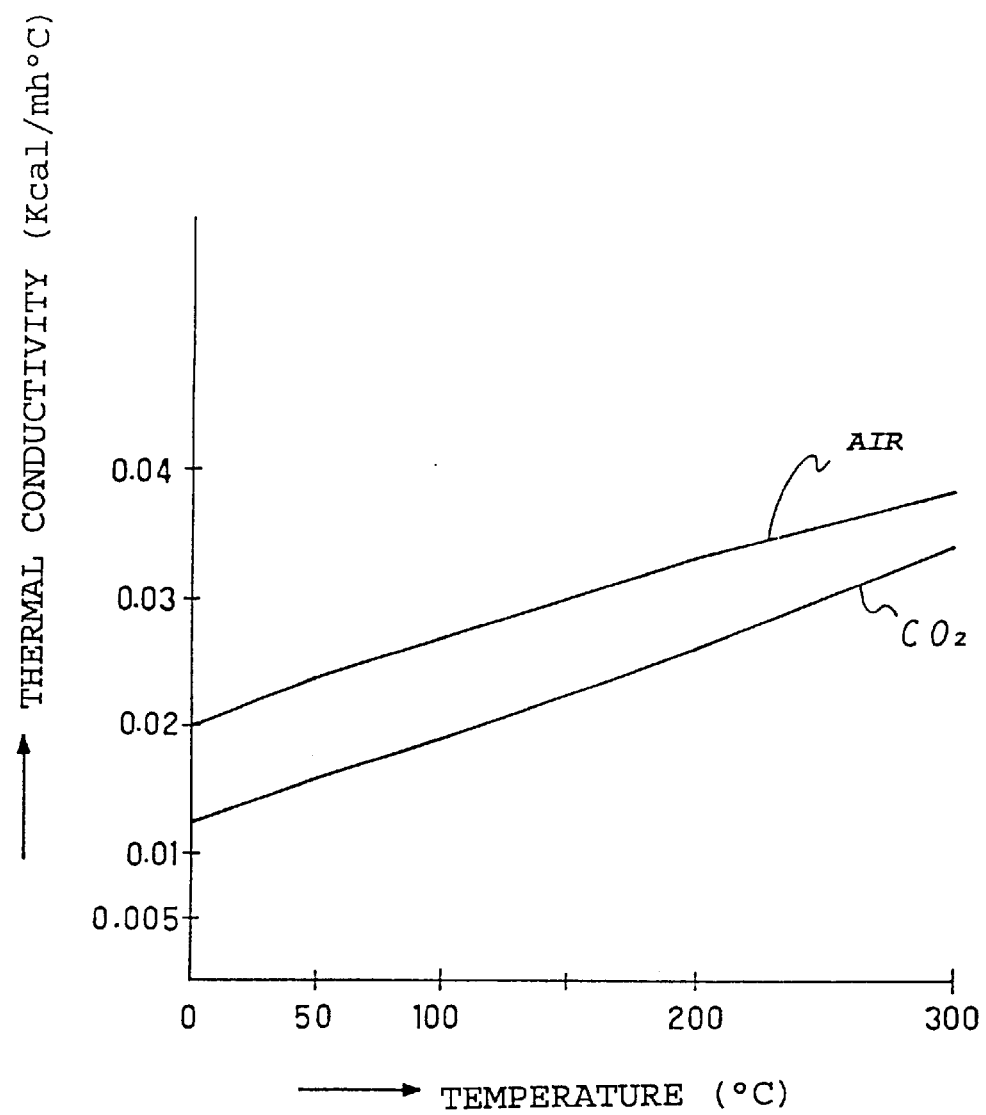
FIG. 10 is a graph showing the relationship between the temperature and the thermal conductivity, illustrating a difference between the atmosphere and the carbon dioxide gas.

On the other hand, the liquefied cooling gas supplied to the cooling chamber 11 is also transformed into the snow dry ice therein, which makes it possible to supply the cooling atmosphere to the interior of the entire casket body 1 through an upper surface of the lower cooling casing 3. Then, the cooling gas thus used enters the interior of the lower ventilation board 4 through the left one (as viewed in FIG. 1) of the ventilation spaces 7 and flows to the right one of the ventilation spaces 7. The cooling gas issued from the right one of the ventilation spaces 7 is then received in the gas recovery tube 21 and discharged from the gas discharge portion 23 to the atmosphere through the suitable filter element (not shown). In operation, the lower ventilation board 4 is filled with the cooling gas, which enables the ventilation board 4 to serve as a sufficient heat insulating means. More particularly, as is clear from the graph shown in FIG. 10, since the cooling gas (i.e., carbon dioxide in the graph) is much lower in thermal conductivity than the atmosphere, the lower ventilation board 4 filled with such cooling gas is excellent in heat insulating properties.

The cooling atmosphere (i.e., carbon dioxide gas) supplied to the cadaver 50 not only cools the cadaver 50 and the interior of the casket, but also sterilizes at least aerobe present therein. As a result, the cadaver 50 is prevented from putrefying under the effect of a so-called "gas pack", which prevents the family of the deceased from secondary infection of such aerobe in case that the family touches the cadaver.

In practical operation in use, when the atmosphere is in the cold of winter, it is possible to eliminate the cooling mechanism installed in the casket body 1. In this case, only the cooling mechanism installed in the lid member 2 is used to consume, for example, 5 Kg of the liquefied cooling gas for every 10 hours. This cooling gts supply is automatically controlled in time and interval by the timers 32, 33 having been previously set. On the other hand, when the atmosphere is in the heat of summer, for example, 10 Kg of the liquefied cooling gas for every 10 hours is supplied to the apparatus of the present invention. In this case, preferably, the casket is previously cooled by a funeral director. In general, a funeral service takes 50 hours in total. Consequently, in summer, the casket containing the cadaver 50 is previously cooled in the place of the funeral director using 10 Kg of the liquefied cooling gas scheduled for 10 hours. Then, in the funeral home, 40 Kg of the liquefied cooling gas scheduled for 40 hours are used, in which 10 Kg of the liquefied cooling gas is supplied to the casket for every 10 hours. Consequently, the total amount of the liquefied cooling gas required in the funeral service in summer reaches 50 Kg.

Figure 5:
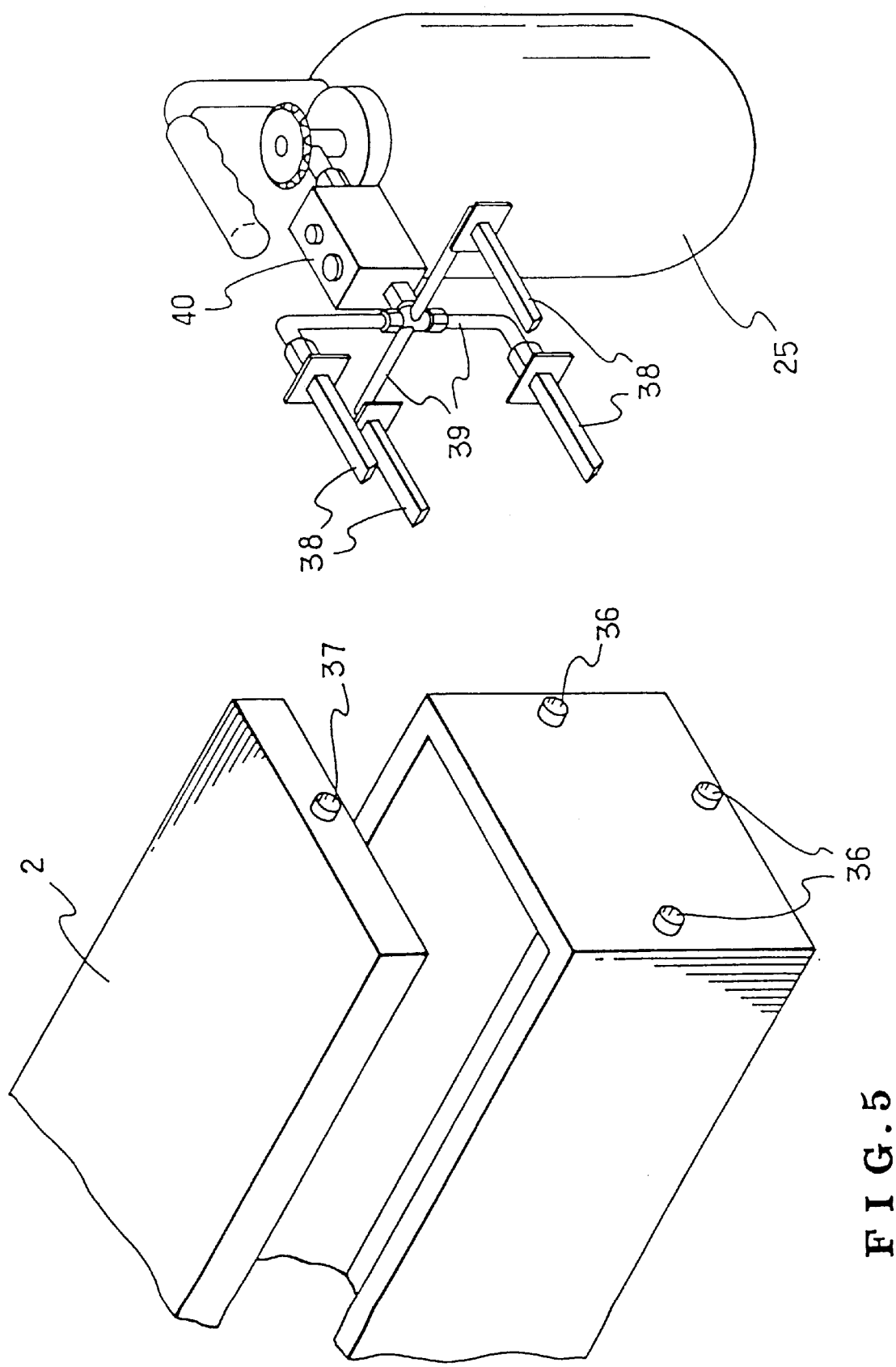
FIG. 5 is a perspective view of another embodiment of the apparatus of the present invention.

A second embodiment of the present invention shown in FIG. 5 is a simplified modification of the first embodiment shown in FIG. 1, and constructed of the casket body 1 and the lid member 2, provided that each of them 1, 2 assumes a hollow shape in the second embodiment.

As shown in FIG. 5, a plurality of gas injection ports 36 are provided in opposite ends of the casket body 1. The lid member 2 is also provided with a plurality of gas injection ports 7 in its opposite ends. These ports 36 and 37 communicate with a hollow portion of the casket body 1 and that of the lid member 2, respectively. Of the gas injection ports 36, two of them are provided in opposite side plates of the casket body I and the remaining one is in a bottom plate of the casket body 1. In this case, as shown in FIG. 5, the cooling gas bomb 25 is connected with a plurality of branch pipes 39 through a timer 40 for controlling in timing the supply of the cooling gas. Each of the branch pipes 39 is provided with an injection nozzle 38 being detachably connected with each of the gas injection ports 36, 37.

FIGS. 6(A) and 6()B) show two methods for connecting the injection nozzle 38 with each of the gas injection ports 36, 37. Of these methods, one shown in FIG. 6(A) uses an externally threaded tubular member 41 which is threadably engaged with each of the gas injection ports 36, 37. The injection nozzle 38 is provided with an internally threaded portion 42 in its front end, and threadably engaged with the tubular member 41 through such threaded portion 42. On the other hand, in the method shown in FIG. 6(B), each of the gas injection ports 36, 37 is provided with a closure plate 43 inside the casket body 1. This closure plate 43 is swingable inwardly when pushed from outside. Consequently, when the injection nozzle 38 is inserted into each of the gas injection ports 36, 37 to push the closure plate 43, the plate 43 is opened to permit the nozzle 38 to enter the hollow portion of each of the casket body 1 and the lid member 2. After completion of gas injection, when the nozzle 38 is pulled out of the ports 36, 37, the closure plate 43 returns to its original position under the effect of a resilient force exerted by a suitable resilient means such as rubber members, spring members and the like, and is therefore brought into close contact with an inner edge portion of each of the gas injection ports 36, 37 to close the same.

Also in the embodiments shown in FIGS. 6(A), 6(B), as is in the above embodiment, the timer 40 controls in timing the supply of the liquefied cooling gas so that the cooling gas is supplied to the hollow portions of the casket body 1 and the lid member 2 at predetermined time intervals, whereby the snow dry ice is formed therein, which makes it possible to keep the interior of the casket cool for a prolonged period of time.

Figure 7:
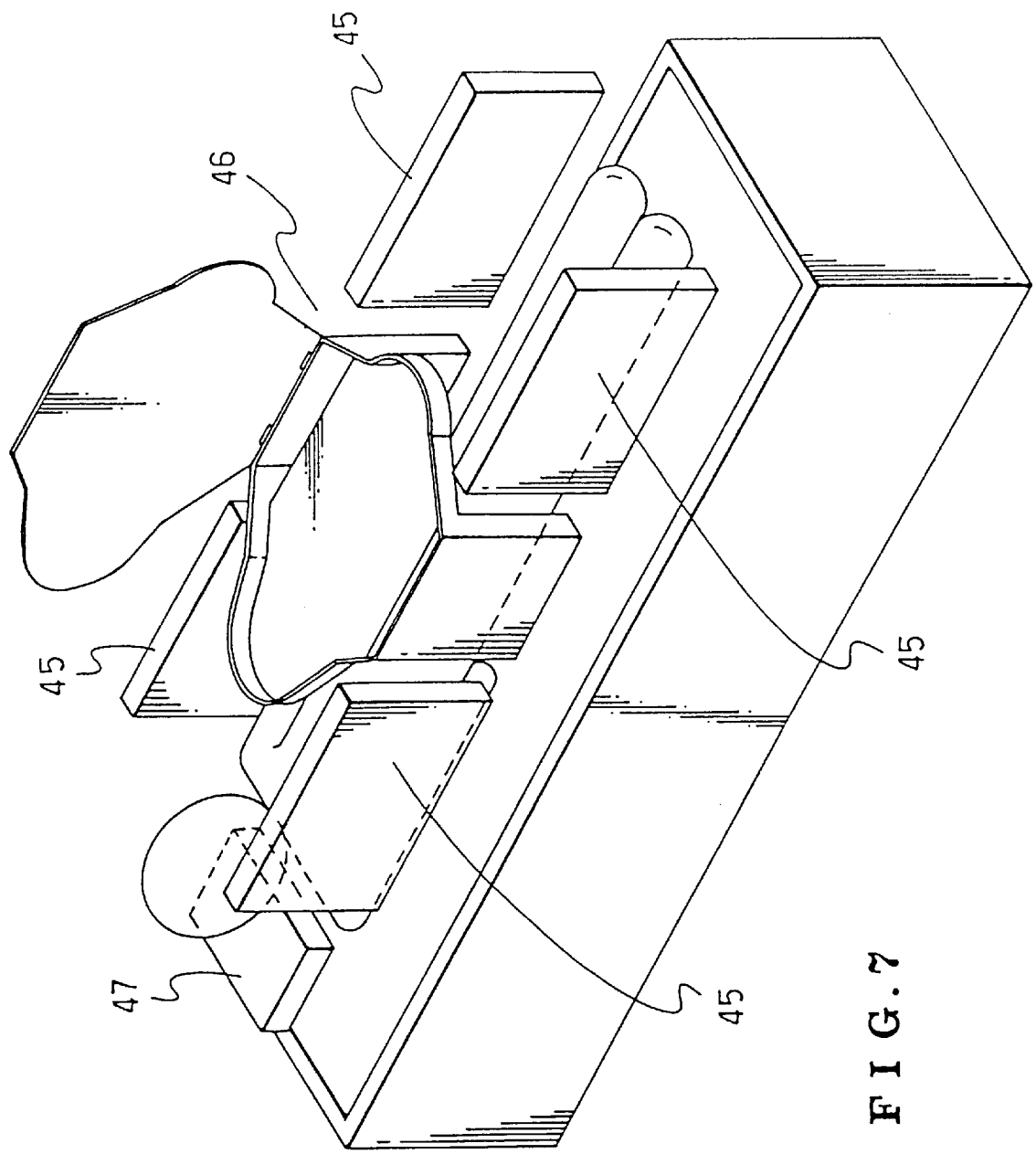
FIG. 7 is a perspective view of a further another embodiment of the apparatus of the present invention.

FIG. 7 shows a third embodiment of the apparatus of the present invention, in which the casket body 1 is provided with: a plurality of refrigerant containing cases 45 in its opposite inner longitudinal sides; a refrigerant containing case 46 in its inner bottom surface adjacent to a head portion of the cadaver 50; and, a refrigerant containing cases 47 in a central area of its upper inner surface, provided that the case 47 has its opposite side portions disposed in the opposite inner Longitudinal sides of the casket body 1, as is clear from FIG. 7. These refrigerant containing cases 45, 4(;, 47 are fixedly mounted in the casket body 1 by means of a suitable fastening means such as adhesive double coated tapes and the like. Of these refrigerant containing cases 45, 46, 47, ones 45 are adjacent to arm and leg portions of the cadaver 50 disposed in the casket body 1 in a supine position; one 46 adjacent to a hip portion of the cadaver 50; and, the remaining one 47 adjacent to a lower side of the head portion of the cadaver 50.

The refrigerant containing case 47 is openable and closable. In preparation, the case 47 is taken out of the casket body 1 and opened, so that a suitable refrigerant such as block-type dry ice, pellet-type dry ice and the like is filled in the case 47. Such refrigerant is adequately controlled in both its amount and its supply interval according to season conditions.

Of these refrigerant containing cases 45, 46, 47, ones 45, 47 may be incorporated in the first embodiment of the present invention shown in FIG. 1. Namely, since the snow dry ice is poor in durability after supplied to the casket, it is preferable to reinforce the snow dry ice in durability in the casket by mounting the refrigerant containing cases 45, 47 in the casket body 1, the cases 45, 47 being filled with the suitable refrigerant such as block-type dry ice, pellet-type dry ice and like.

Figure 8:
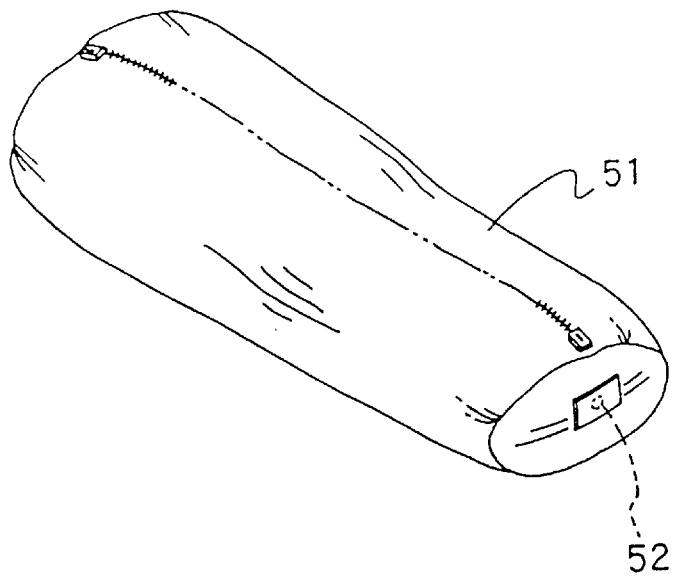
FIG. 8 is a perspective view of a still further another embodiment of the apparatus of the present invention.

FIG. 8 shows a corpse-containing disaster pouch 51 which contains a cadaver 50 therein. In general, the disaster pouch 51 is hermetically constructed of double-walled heat insulating materials, and provided with a liquefied cooling gas supply port 52. The liquefied cooling gas is supplied to the interior of the disaster pouch 51 through this port 52 at predetermined intervals, and transformed into the snow dry ice therein.

The disaster pouch 51 may be modified in construction so as to be constructed of a single-walled heat insulating material. It is also possible to directly supply the liquefied cooling gas to the interior of such modified disaster pouch 51. This is particularly effective to treat many victims of a disaster or a considerably putrefied cadaver in the field. In this case, the liquefied cooling gas is brought into direct contact with the cadaver 50 so that the cadaver 50 is covered with the snow dry ice (i.e., one such as solid carbon dioxide) and the cooling gas. As a result, it is possible to prevent the cadaver 50 from further putrefying, and to obtain a so-called "gas pack" effect on the cadaver 50.

Figure 9:
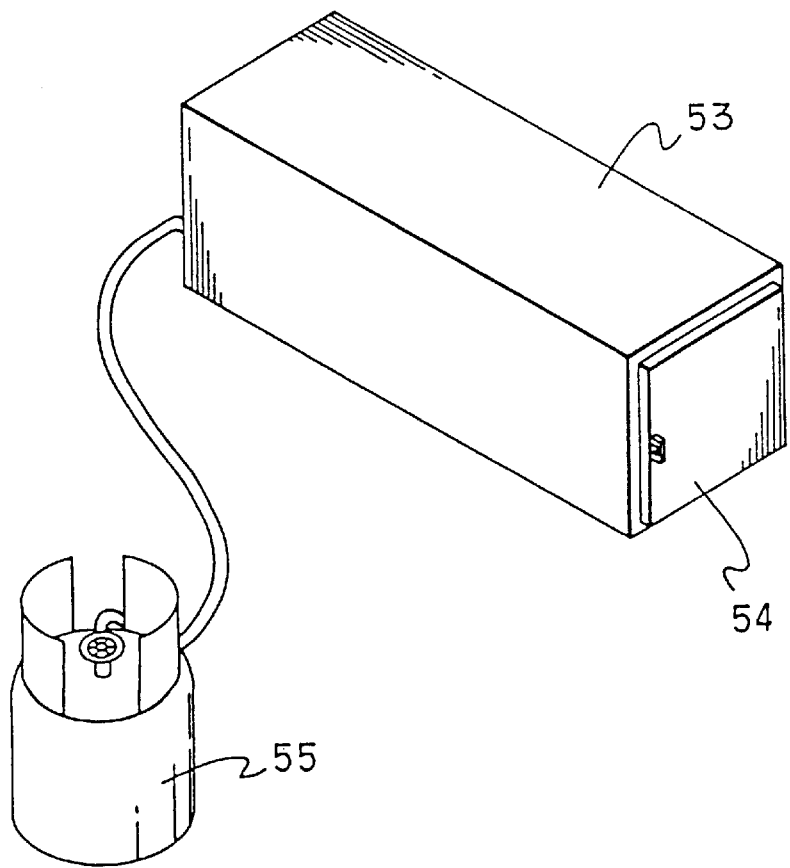
FIG. 9 is a perspective view of another embodiment of the apparatus of the present invention.

FIG. 9 shows a cooling box 53 provided with a lid member 54. In preparation, the lid member 54 is opened, so that the casket or disaster pouch 51 containing the cadaver 50 is placed therein and cooled there. The cooling box 53 is connected with a liquefied cooling gas bomb 55, as shown in FIG. 9.

Incidentally, in any of the above embodiment of the present invention, it is possible, as a means for discharging the used cooling gas, to use a suitable discharge port in place of the double-walled nozzle shown in FIG. 4, the discharge port being directly formed in the casket or disaster pouch.

In the method of the present invention for conserving the cadaver used in place of the conventional embalming: the liquefied cooling gas is supplied to the cadaver 50 through its opening portions, which comprise the oral cavity, nasal cavity, auditory meatus, anus and like openings in addition to artificial cuts and accidentally damaged portions of the cadaver 50 in its inside (i.e., viscera) and outside. More particularly, the liquefied cooling gas, which is highly pressurized, is injected into the cadaver 50 through the gas injection nozzle which corresponds in shape to the opening portion of the cadaver 50.

The liquefied cooling gas used in the above may be of nitrogen or carbon dioxide. In case of carbon dioxide gas is used, a part of such highly pressurized gas is transformed into the snow dry ice immediately after injected into the cadaver 50 through its oral cavity, and filled in every victus communicating with the airway and the esophagus of the cadaver 50.

Since a human body is a so-called tubular body, all the digestive wastes remaining inside the cadaver 50 are forcibly discharged front the inside of the cadaver 50 through its rectum and anus portions under the effect of high pressure of the cooling gas injected therein. The cooling gas thus filled in the cadaver 50 sterilizes bacteria therein, and spreads itself through the entire muscles rapidly, whereby the cadaver 50 is cleaned and conserved for a long period of time. Namely, the cooling gas is filled in every nook and corner of the intestinal cavities of the cadaver 50 to rapidly cool the cadaver 50 from its inside, and keeps the cadaver 50 at low temperatures of several degrees centigrade.

When the liquefied cooling gas is injected into the cadaver 50, all the lungs, stomach and the intestines are inflated with the cooling gas. Under such circumstances, when the cadaver 50 is pressed by hands, the gas filled in the cadaver is easily discharged therefrom. As a result, the cadaver 50 may return to its normal condition after completion of injection of the cooling gas. Further, it is also possible to supply the liquefied cooling gas to the head or brain portion of the cadaver 50 by changing the gas injection nozzle in shape. Incidentally, when the liquefied cooling gas emits a loud noise when injected into the cadaver 50, the noise level thereof may be depressed by mounting a suitable silencer or muffler on the gas injection nozzle.

Further, in the method of the present invention, it is also possible to supply a coloring or color producing gas colored red or like warm colors to the cadaver 50 through an incision in its blood vessel: generally the carotid artery. In this case, the cadaver 50 may show the appearance of the live person in its skin. The color producing gas described above is a kind of mixture gas composed of oxygen and carbon dioxide, which gas is generally used for keeping beef and like animal meets reddish and fresh. It is also possible to supply a suitable aroma gas to the cadaver 50 through its opening portion or blood vesse Is.

As described above, the method of the present invention may conserve the cadaver 50 for a prolonged period of time by cooling the cadaver 50 from inside. Though the method itself is sufficiently effective in practice, it may be combined with the other method for cooling the interior of the casket described above.

Incidentally, when the viscera portion of the cadaver is crushed so that the cadaver is damaged, the viscera portion thus crushed may be replaced with a suitable packing. Also to such case, the present invention may be applied.

In the present invention described above, it is possible to keep the interior of the casket containing the cadaver therein at a suitable low temperature ranging from 3 to 5 degrees centigrade under the effects of the cooling gas: the refrigerating effect and the heat insulating effect. Consequently, the present invention may prevent the cadaver from putrefying so as to prevent foul odors, and may keep the cadaver fresh as if it still lives in appearance. Further, since the cooling gas may sterilize bacteria, it is possible to prevent a secondary infection of contagium when the family touches the cadaver.

Particularly, in the method of the present invention as set forth in the first aspect of the present invention, the use of block-type dry ice in addition to the use of liquefied cooling gas may help control in temperature the interior of the casket. The apparatus of the present invention is constructed of combustible materials, and, therefore suitable for cremation together with the casket.

In the method of the present invention for cleaning and conserving the cadaver, though the cadaver is carried in and out of the casket by hands, it is not required to cut the cadaver, or remove the viscera thereof, in contrast with embalming services. The method of the present invention may utilize beneficial properties of the liquefied cooling gas (particularly, of liquefied carbon dioxide gas) to control in freshness, in temperature and in sterilization the casket containing the cadaver in an easiest manner. Further, the method of the present invention may remove the digestive wastes from the inside of the cadaver using the gas pressure to clean the cadaver, which enables the cadaver to keep the appearance of the live person for a long period of time.

Finally, the method of the present invention is very simple in operation, and does not require any sophisticated techniques, which cuts time and labor to reduce installation costs. In addition, in the method of the present invention, the cadaver is substantially not damaged, which eases the family's mind of the deceased. Consequently, the present invention will be widely carried out.

What is claimed is:

1. A method for conserving a cadaver comprising the steps of:

providing a casket enclosing the cadaver;

forming a liquefied cooling-gas supply space in the casket separated by at least one solid planar wall from a space enclosing the cadaver, and supplying a liquefied cooling gas to said liquefied cooling-gas supply space;

whereby the space enclosing the cadaver of said casket is cooled and sterilized through said at least one solid planar wall.

2. The method for conserving the cadaver, as set forth in claim 1, wherein:

said liquefied cooling gas is supplied to said liquefied cooling-gas supply space at predetermined time intervals.

3. The method for conserving the cadaver, as set forth in claim 1, wherein:

an amount of said liquefied cooling gas necessary for conserving the cadaver for a predetermined period of time is supplied to said liquefied cooling-gas supply space at a time.

4. The method for conserving the cadaver, as set forth in claim 1, wherein:

block-type or pellet-type dry ice is disposed inside said casket to serve as an auxiliary cooling means.

5. In an apparatus for conserving a cadaver, including a casket having a casket body lid member and an improvement comprising cooling means in the casket for conserving the cadaver therein;

said cooling means having a cooling casing separated by at least one solid planar wall plate from a space enclosing the cadaver;

a nozzle member for supplying and communicating a liquefied cooling gas to an interior of said cooling casing.

6. The apparatus for conserving the cadaver, as set forth in claim 5, wherein;

at least one ventilation board having an interior to permit distribution of the liquified cooling gas is housed in said cooling casing; and a cooling chamber is formed between said ventilation board and said solid planar wall plate of said cooling casing to permit said liquefied cooling gas to pass through said cooling chamber and enter an opening to the interior of said ventilation board and flow therein in a direction opposite to that of said liquefied cooling gas when flowing through said cooling chamber and after said cooling gas flows through the interior of said ventilation board exiting to an exterior of said casket.

7. The apparatus for conserving the cadaver, as set forth in claim 6, wherein:

said cooling chamber is formed in said lid member of said casket on said solid planar wall plate which is a bottom wall of said cooling casing;

an opening is formed in a central area of said bottom wall plate of said cooling casing; and a snow-receiving means, which is made of permeable materials, is disposed in said opening.

8. The apparatus for conserving the cadaver, as set forth in claim 7, wherein:

a cooling hole for permitting a cooling effect of said cooling chamber to be transmitted into said casket is formed in said solid planar wall plate of said cooling casing at a position corresponding to an outer periphery of a head portion of said cadaver.

9. The method for conserving the cadaver, as set forth in claim 1, wherein said casket is a corpse containing pouch.

10. The apparatus for conserving the cadaver as set forth in claim 5, wherein said cooling chamber houses a plurality at said ventilation board.

* * * * *